(12) United States Patent  
Morgan

(10) Patent No.: US 9,107,693 B2
(45) Date of Patent: Aug. 18, 2015

(54) APPARATUS AND METHOD FOR PERICARDIAL ACCESS

(75) Inventor: Kevin L. Morgan, Simi Valley, CA (US)

(73) Assignee: PACESETTER, INC., Sylmar, CA (US)

( * ) Notice: Subject to any disclaimer, the term of this patent is extended or adjusted under 35 U.S.C. 154(b) by 423 days.

(21) Appl. No.: 13/448,196

(22) Filed: Apr. 16, 2012

(65) Prior Publication Data

US 2013/0274782 A1     Oct. 17, 2013

(51) Int. Cl.
*A61B 17/34* (2006.01)
*A61B 17/00* (2006.01)

(52) U.S. Cl.
CPC ............. *A61B 17/34* (2013.01); *A61B 17/3468* (2013.01); *A61B 2017/00243* (2013.01); *A61B 2017/3458* (2013.01); *A61B 2017/3488* (2013.01)

(58) Field of Classification Search
CPC ........ A61B 17/32; A61B 19/00; A61B 17/22; A61B 17/3415; A61B 17/3417; A61B 2017/3454; A61B 2017/3456; A61B 2017/00247; A61B 17/32113; A61B 17/3496; A61B 5/15; A61B 2017/00336; A61B 17/34; A61B 17/3468; A61B 2017/3488; A61B 2017/00243; A61B 2017/3458; A61M 25/06; A61M 25/0612; A61M 25/0631; A61M 25/0662; A61M 2025/0687; A61M 2005/2013
USPC ........................ 606/166–188, 301, 304, 108; 600/566–567; 604/164.01, 164.06, 604/164.1, 164.11–164.12, 117
See application file for complete search history.

(56) References Cited

U.S. PATENT DOCUMENTS

| | | | | |
|---|---|---|---|---|
| 5,047,040 A | * | 9/1991 | Simpson et al. | 606/159 |
| 5,569,197 A | * | 10/1996 | Helmus et al. | 604/102.02 |
| 6,015,391 A | * | 1/2000 | Rishton et al. | 600/567 |
| 6,123,084 A | * | 9/2000 | Jandak et al. | 128/898 |
| 6,443,966 B1 | * | 9/2002 | Shiu | 606/159 |
| 7,771,411 B2 | * | 8/2010 | Smith et al. | 604/525 |
| 7,905,897 B2 | * | 3/2011 | Whitman et al. | 606/172 |
| 8,201,563 B2 | * | 6/2012 | Conquergood et al. | 128/898 |
| 2004/0199236 A1 | | 10/2004 | Laske et al. | |
| 2009/0018468 A1 | * | 1/2009 | Janssens | 600/567 |
| 2009/0143698 A1 | * | 6/2009 | Janssens | 600/566 |
| 2010/0016878 A1 | * | 1/2010 | Smith | 606/185 |
| 2010/0160719 A1 | | 6/2010 | Kassab et al. | |
| 2011/0112434 A1 | * | 5/2011 | Ghabrial et al. | 600/564 |
| 2012/0143232 A1 | * | 6/2012 | Gedet et al. | 606/167 |

* cited by examiner

*Primary Examiner* — Amy R Weisberg

(57) ABSTRACT

Implementations described and claimed herein provide controlled access into the intra-pericardial space. In one implementation, a medical device comprises an outer sheath, an inner sheath, and a nose shaft. The outer sheath comprises a proximal end, a distal end, and a lumen extending between the proximal end and the distal end. The inner sheath extends through the lumen of the outer sheath and comprises a distal portion adapted to pierce the pericardial sac. The nose shaft is adapted to displace relative to a distal edge of the distal portion of the inner sheath. Displacing the distal portion of the inner sheath relative to the outer sheath until the nose shaft displaces relative to the distal edge provides controlled penetration into the intra-pericardial space.

5 Claims, 10 Drawing Sheets

APPARATUS AND METHOD FOR PERICARDIAL ACCESS

FIELD OF THE INVENTION

The presently disclosed technology relates to medical apparatuses and methods. More specifically, the presently disclosed technology relates to an apparatus and a method for accessing an intra-pericardial space.

BACKGROUND OF THE INVENTION

The heart is enveloped within a tissue membrane structure known as the pericardium or pericardial sac. The pericardium consists of two layers, the fibrous pericardium and the parietal pericardium, which is a serous lining adjacent to the fibrous pericardium. In some instances reference is made to a third visceral pericardial layer, the epicardium, which is the layer on the surface of the myocardium. Between the pericardial sac and the surface of the heart is an intra-pericardial space. Approximately 15 to 35 milliliters of serous fluid fills the intra-pericardial space, providing lubrication and protection for the heart.

For patients in need of cardiac rhythm treatment (CRT), a minimally invasive pericardial approach to placing a stimulating lead (e.g., a chronic cardiac pacing lead) has recently been used as an alternative to transvenous and invasive surgery methods. In the pericardial approach, doctors access the intra-pericardial space to place a stimulating lead on the epicardial surface. Needle and needle-like tools are generally used to gain access to the intra-pericardial space.

For example, some of these tools employ a distal suction cup to stabilize the pericardial sac while a needle punctures the pericardial sac and enters the intra-pericardial space. However, there is difficulty maintaining a vacuum to stabilize the pericardial sac and the diameter of a percutaneous port in these tools must be sufficiently large (e.g., 18 French diameter or larger). Many other tools access the intra-pericardial space by grabbing and stabilizing the pericardial sac while a needle is advanced into the pericardial space. Such tools may grab the pericardial sac, for example, using clips or pinchers. However, such tools often encounter challenges to accessing the intra-pericardial space when obstructions to the pericardial sac are present. For example, the pericardial sac is covered in a layer of fat, which varies in thickness from patient to patient.

In another approach that is unaffected by the layers of fat surrounding the pericardial sac, doctors gain percutaneous access into the intra-pericardial space using a sub-xiphoid puncture technique employing an epidural Touhy needle, for example, a 17-gauge Touhy needle. Visualization techniques, such as fluoroscopy, MRI, echocardiography, or endoscopy are generally used to guide the needle to an implantation location within the intra-pericardial space and to guide positioning of the stimulating lead. Contrast media may be used during puncture to determine if the needle has passed through the pericardial sac and is correctly positioned in the intra-pericardial space. However, such techniques pose the risks of the needle puncturing the myocardium, entering the heart chambers, and causing excessive bleeding.

Specifically, for patients with a relatively normal pericardial sac, gaining access into the intra-pericardial space using a needle is difficult. This difficulty arises because: the pericardial sac is generally a thin tough connective tissue with little stretchability; the pericardial sac is slippery on, and slides over the heart wall; and the virtual space available for puncture provides little puncture room for pressing the needle into the pericardial sac. The term "virtual space" refers to the potential space between the two extreme limits of the epicardial surface and the pericardial sac. The challenges of accessing the intra-pericardial space can easily result in the heart wall being punctured, increasing the risk for tamponade (i.e., compression of the heart by an accumulation of fluid or blood in the pericardial sac).

Accordingly, there is a need in the art for a method and apparatus that will facilitate accessing the intra-pericardial space while reducing the risk of puncturing the heart wall.

BRIEF SUMMARY OF THE INVENTION

Implementations described and claimed herein address the foregoing problems by providing controlled access into the intra-pericardial space. In one implementation, a medical device comprises an outer sheath, an inner sheath, and a nose shaft. The outer sheath comprises a proximal end, a distal end, and a lumen extending between the proximal end and the distal end. The inner sheath extends through the lumen of the outer sheath and comprises a distal portion adapted to pierce the pericardial sac. The nose shaft is adapted to displace relative to a distal edge of the distal portion of the inner sheath. Displacing the distal portion of the inner sheath relative to the outer sheath until the nose shaft displaces relative to the distal edge provides controlled penetration into the intra-pericardial space.

Another implementation provides a method for controlled access into the intra-pericardial space. The method comprises positioning a distal portion of an inner sheath in close proximity to a pericardial sac. The inner sheath is located in an outer sheath. The pericardial sac is engaged with a hook on the distal portion of the inner sheath. The inner sheath is displaced relative to the outer sheath until an indicator located on a proximal portion of a nose shaft displaces relative to a proximal end of the outer sheath. The displacement of the indicator identifies when a distal tip of the nose shaft is positioned in the intra-pericardial space.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

DETAILED DESCRIPTION

Aspects of the presently disclosed technology involve a device and method for controlled access into an intra-pericardial space. In one implementation, the device includes an outer sheath and an inner sheath extending through a lumen of the outer sheath. The inner sheath comprises a distal portion adapted to pierce the pericardial sac. The device further includes a nose shaft adapted to displace relative to a distal edge of the distal portion of the inner sheath.

The device may be inserted into a patient, for example, via a sub-xiphoid access, a transthoracic keyhole access, or other minimally invasive access. After insertion, the distal portion of the inner sheath is positioned against a surface of the patient's pericardial sac such that a hook on the distal portion of the inner sheath engages the pericardial sac. The inner sheath is displaced relative to the outer sheath until an indicator located on a proximal portion of the nose shaft displaces distally relative to a proximal end of the middle sheath. The displacement of the indicator identifies when a distal tip of the nose shaft is positioned in the intra-pericardial space, thereby providing controlled access to the intra-pericardial space.

The device and method provide a precise, controlled puncture of the pericardial sac with little risk of puncturing the heart surface. Thus, the device and method are advantageous because they are unaffected by obstructions located on the pericardial sac (e.g., fat), eliminate tenting of the pericardium, eliminate the need for a needle to puncture the pericardial sac, increase the predictability of procedures involving access to the intra-pericardial space (e.g., implant procedures), reduce implant time and fluoroscopy time, and allow the pericardial sac to be punctured in all four chamber zones of the heart.

Figure 1:
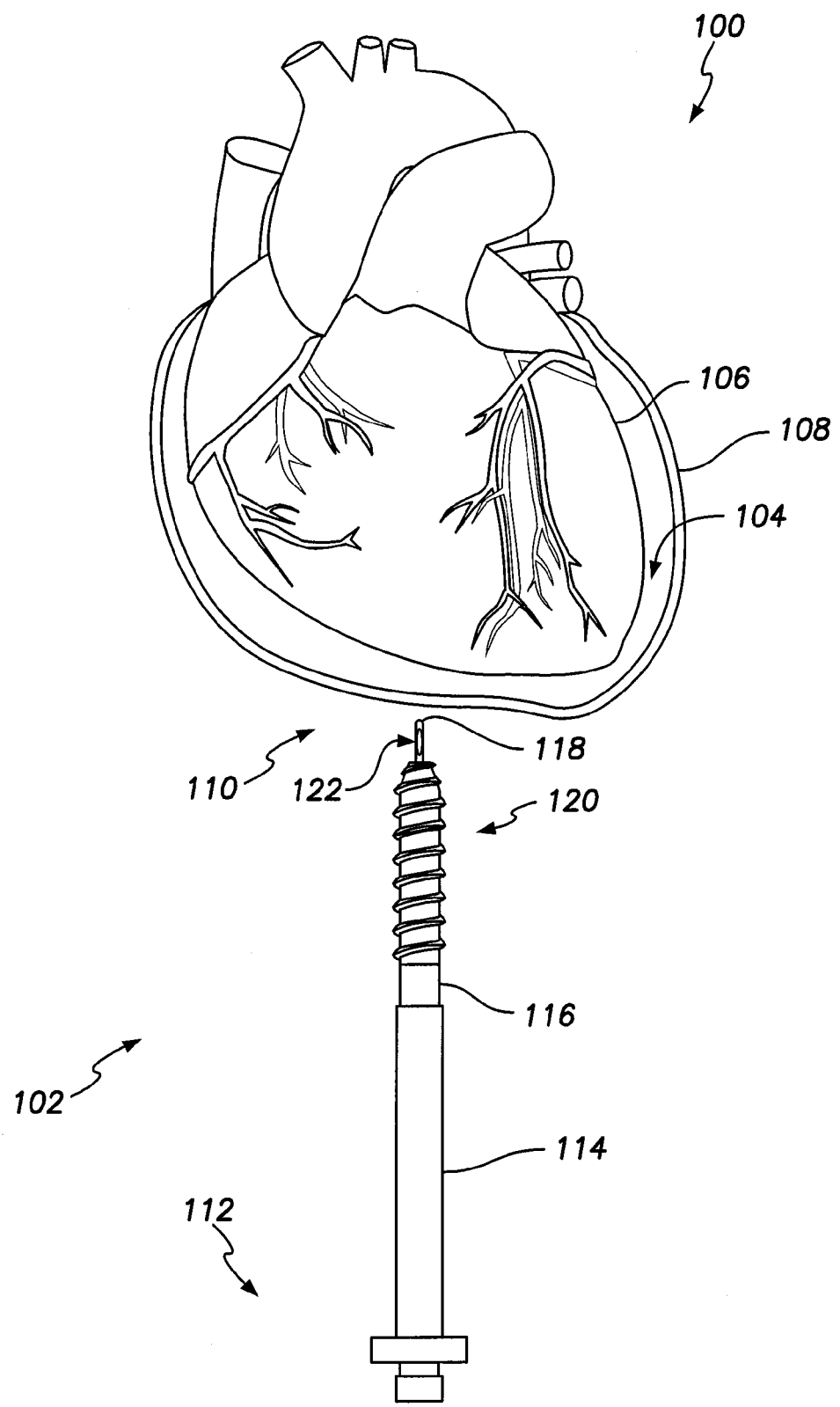
FIG. 1 illustrates a schematic representation of an implementation of a device being employed for controlled access into intra-pericardial space.

For a detailed discussion of an implementation of the device and method, reference is made to FIG. 1, which is a schematic representation 100 of an implementation of a device 102 being employed for controlled access into an intra-pericardial space 104. As shown in FIG. 1, the intra-pericardial space 104 is the space between the heart surface 106 and the pericardial sac 108. After the device 102 is inserted into a patient, a distal end 110 of the device 102 is positioned in close proximity to the pericardial sac 108 and a proximal end 112 of the device 102 extends from the patient such that an implanter (e.g., a doctor) may control the operation of the device 102. An example implementation of the device 102 inserted into a patient may be understood from FIG. 6.

In one implementation, the device 102 includes an outer sheath 114, an inner sheath 116 extending through a lumen of the outer sheath 114, and a nose shaft 118 extending through a lumen of the inner sheath 116. A distal portion 120 of the inner sheath 116 is adapted to pierce the pericardial sac 108 and advance the distal end 110 of the device 102 into the intra-pericardial space 104. Stated differently, the distal portion 120 of the inner sheath 116 is displaced distally relative to the outer sheath 114 to advance the distal end 110 of the device 102 through the pericardial sac 108. Once the distal portion 120 of the inner sheath 116 is positioned in the intra-pericardial space 104, the nose shaft 118 is displaced distally relative to the inner sheath 116. The displacement of the nose shaft 118 notifies the implanter that the distal end 110 of the device 102 is positioned in the intra-pericardial space 104 and that no further advancement is needed. This notification ensures an implanter does not continue to advance the distal end 110 of the device 102 into the heart surface 106. Additionally, in one implementation, the nose shaft 118 distally terminates with a blunt or otherwise atraumatic surface to prevent the distal portion 120 of the inner sheath 116 from piercing the heart surface 106.

An opening 122 exists in a wall of the nose shaft 118 near the distal end 110 of the device 102 and exposes a lumen of the nose shaft 118, through which a guidewire or other medical device may be deployed into the intra-pericardial space 104 once the distal end 110 of the device 102 is positioned in the intra-pericardial space 104. With the guidewire or other medical device in place, the device 102 may be removed and catheters or introducers with dilators may be advanced over the guidewire into the intra-pericardial space 104 during procedures, including without limitation, implants, surgeries, diagnostics, therapies, reduced patient trauma, and other minimally invasive procedures.

Figure 2:
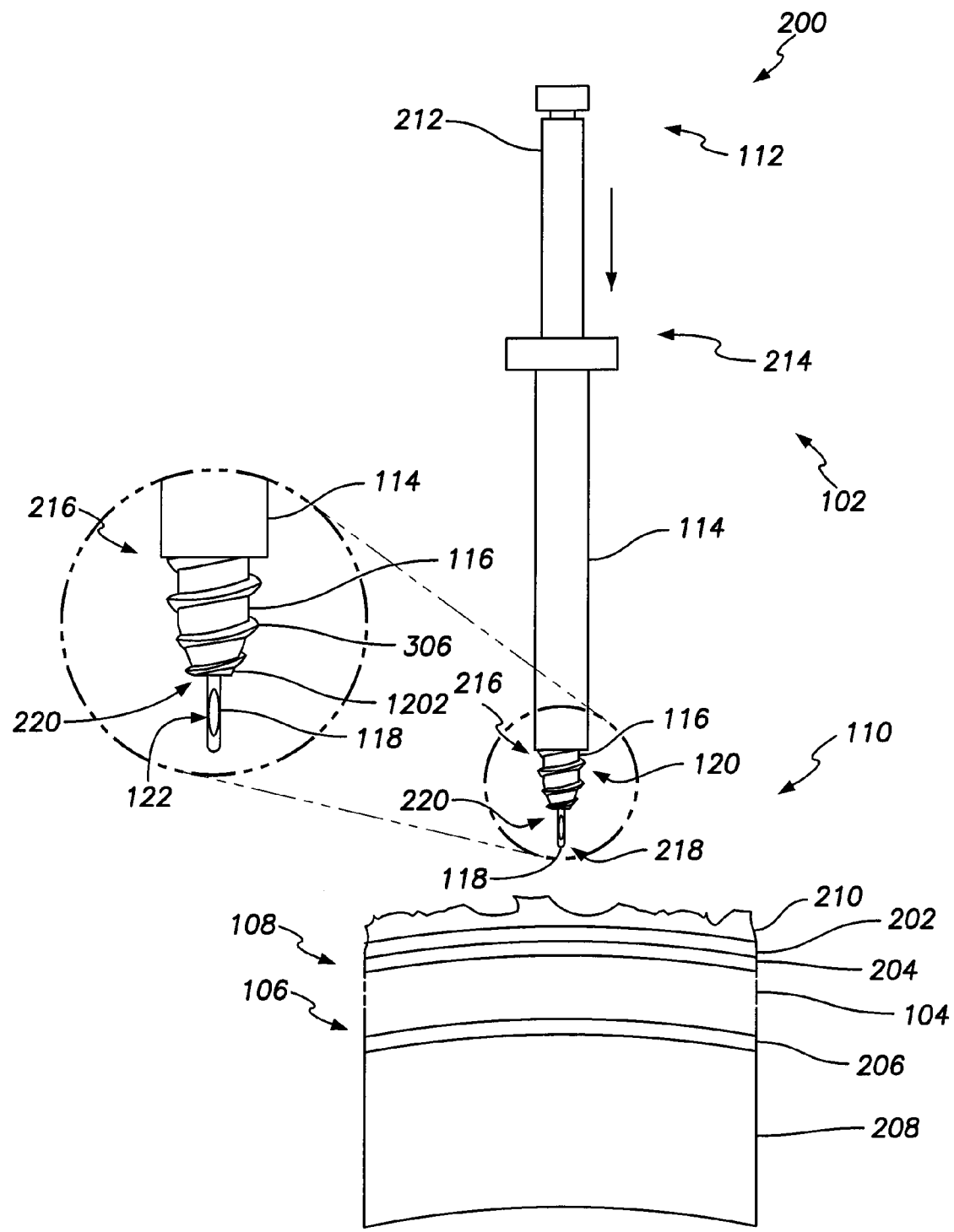
FIG. 2 illustrates a longitudinal sectional side view of an implementation of the device positioned in close proximity to a pericardial sac.

As can be understood from FIGS. 2-5, which are longitudinal sectional side views 200, 300, 400, and 500 of an implementation of the device and method, the device 102 is adapted to provide controlled access to the inter-pericardial space 104. As shown in FIG. 2, the distal end 110 of the device 102 is positioned in close proximity to the pericardial sac 108. The pericardial sac 108 consists of two layers, the fibrous pericardium 202 and the parietal pericardium 204, which is a serous lining adjacent to the fibrous pericardium 202. Often, the fibrous pericardium 202 is covered in a layer of fat 210, which varies in thickness from patient to patient. In some instances reference is made to the heart surface 106, illustrated in FIG. 2 as the epicardium 206, which is the layer on the surface of the myocardium 208. Between the parietal pericardium 204 and the epicardium 206 is the intra-pericardial space 104.

In one implementation, the distal portion 120 of the inner sheath 116 is longitudinally displaceable within the lumen of the outer sheath 114. As depicted in FIG. 2, a middle sheath 212 that connects to the inner sheath at the proximal end is adapted to displace distally, as shown in FIG. 2 by the bolded arrow, causing the distal portion 120 of the inner sheath 116 to distally displace longitudinally relative to the outer sheath 114. Stated differently, the middle sheath 212 is displaced distally into a proximal end 214 of the outer sheath 114 causing the distal portion 120 of the inner sheath 116 to extend from a distal end 216 of the outer sheath.

The nose shaft 118 distally terminates with a distal tip 218, which is a blunt surface. In one implementation, the distal tip 218 of the nose shaft 118 is spring loaded so as to remain protruding out of a distal edge 220 of the inner sheath 116 until the distal tip 218 is met with resistance from the fibrous pericardium 202 and/or the fat layer 210.

Figure 3:
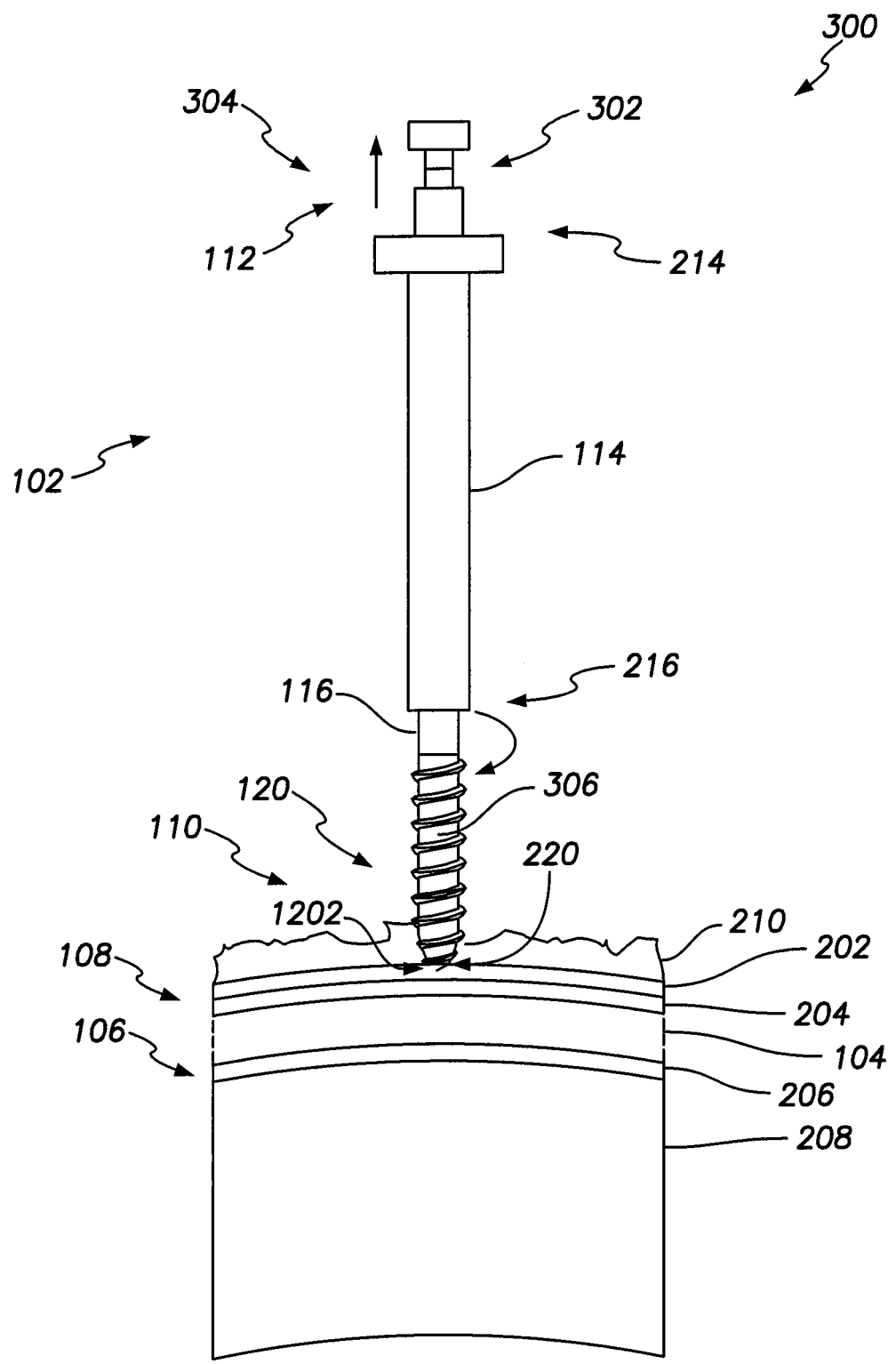
FIG. 3 illustrates the same view as FIG. 2, except the device has engaged the pericardial sac.

As depicted in FIG. 3, the device 102 is adapted to longitudinally displace the inner sheath 116 until the distal portion 120 of the inner sheath 116 engages the pericardial sac 108. In one implementation, the distal tip 218 of the nose shaft 118 is adapted to proximally displace relative to the distal edge 220 of the inner sheath 116 when met with resistance from body tissue. For example, when the distal tip 218 is met with resistance from the fibrous pericardium 202 and/or the fat layer 210, the distal tip 218 retracts into the distal portion 120 of the inner sheath 116, as shown in FIG. 3. The displacement of the distal tip 218 causes an indicator 302 located on a proximal portion 304 of the nose shaft 118 to displace proximally relative to the proximal end of the middle sheath 212 that is connected to the inner sheath 116, as shown in FIG. 3 by the bolded linear arrow. In one implementation, the indicator 302 is a red colored band. However, other colors, designs, and visuals are contemplated. The indicator 302 notifies the implanter that the distal tip 218 of the nose shaft 118 has met resistance from body tissue, such as the pericardial sac 108, and is thus retracted.

The displacement of the distal tip 218 of the nose shaft 118 into the distal portion 120 of the inner sheath 116 causes the distal edge 220 of the inner sheath 116 to become a leading distal edge or point of the device 102. As discussed in detail later in this Detailed Description, a hook 1202 that is located on the distal edge 220 is exposed on the distal portion 120 by the nose shaft 118 displacing into the inner sheath 116, the hook 1202 thereby being positioned and adapted to engage the pericardial sac 108. In one implementation, the distal portion 120 includes helical spiral threads 306 having a cutting surface connected to the hook 1202, the hook 1202 being an extension of at least one thread. In one implementation, the helical spiral threads 306 and the inner sheath 116 taper down distally. When the indicator 302 notifies the implanter that the distal tip 218 of the nose shaft 118 is retracted, the inner sheath 116 is axially rotated by way of the middle sheath 212 causing the inner sheath 116 to longitudinally and rotationally displace relative to the outer sheath 114. As a result, the hook 1202 engages and cuts the fat layer 210 and the pericardial sac 108, the helical spiral threads on the distal portion 120 feeding the fat layer 210 and the pericardial sac 108 along the inner sheath 116 as the hook 1202 and distal edge 220 cut through the tissue. In one implementation, the inner sheath 116 is axially rotated in a clockwise motion, as illustrated in FIG. 3 by the bolded arrow. Those skilled in the art will understand that the piercing of the pericardial sac 108 in this manner provides precise, controlled access to the intra-pericardial space 104 and that tenting of the pericardial sac 108 is significantly reduced.

Figure 4:
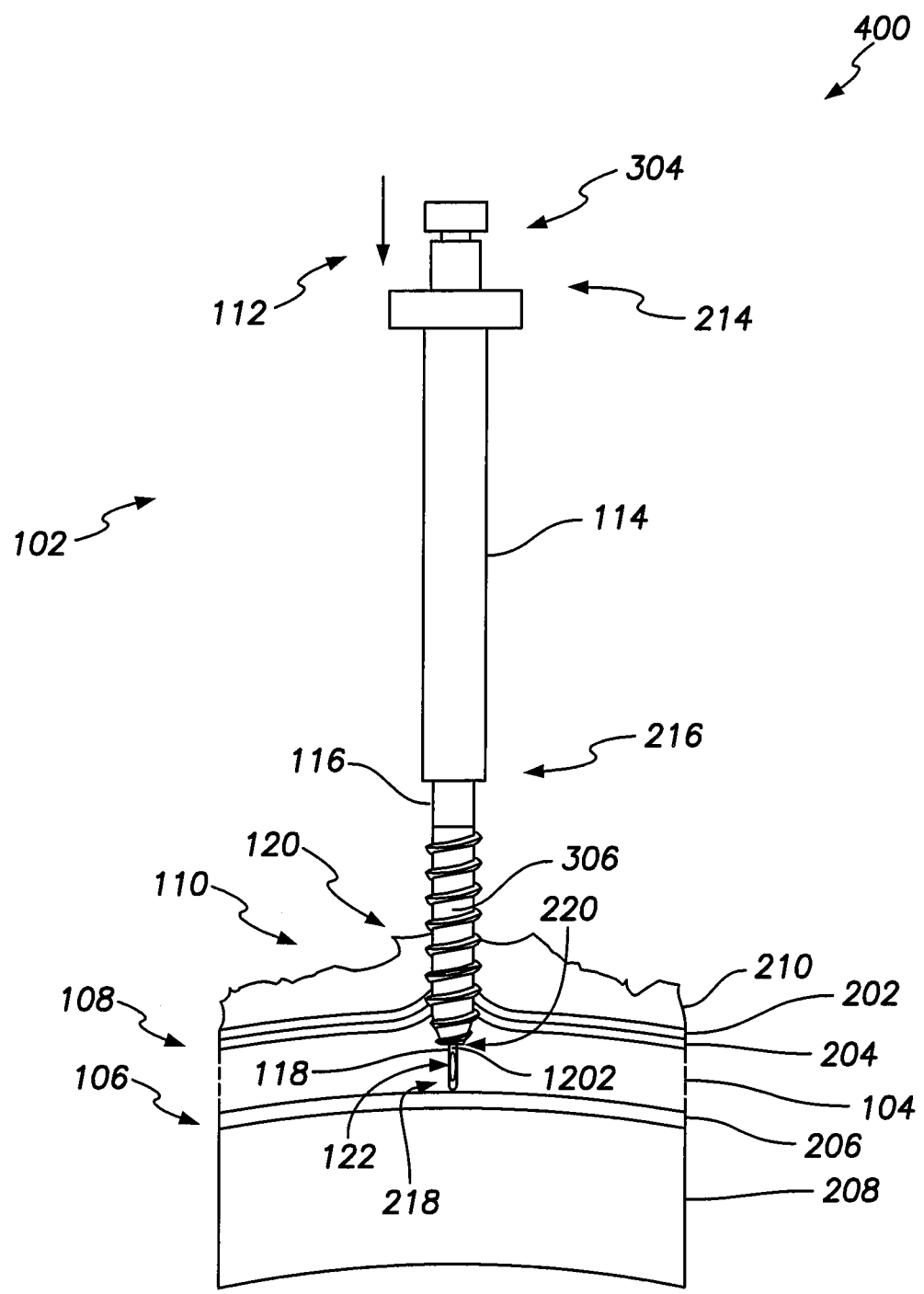
FIG. 4 illustrates the same view as FIG. 2, except the distal tip of the nose shaft is positioned in the intra-pericardial space.

FIG. 4 illustrates the distal tip 218 of the nose shaft 118 positioned in the intra-pericardial space 104. Once the distal portion 120 of the inner sheath 116 pierces the fat layer 210, the fibrous pericardium 202, and the parietal pericardium 204 and enters the intra-pericardial space 104, the distal tip 218 of the nose shaft 118 displaces distally relative to the distal edge 220 of the inner sheath 116, as shown by the bold arrow in FIG. 4 positioned near the distal tip 218. In one implementation, the distal tip 218 distally springs back into a position such that the distal tip 218 protrudes from the distal edge 220 of the inner sheath 116, as discussed with respect to FIG. 2, before the distal tip 218 was met with resistance from body tissue. The displacement of the distal tip 218 causes the indicator 302 to displace distally relative to the proximal end of the middle sheath 212 that is connected to the inner sheath 116, as shown by the bold arrow in FIG. 4 positioned at the proximal end 112 of the device 102. In one implementation, the indicator 302 is retracted distally into the proximal end of the middle sheath 212 that is connected to the inner sheath 116, such that the indicator 302 is not visible, as illustrated in FIG. 4. The displacement of the indicator 302 identifies when the distal tip 218 of the nose shaft 118 is positioned in the intra-pericardial space 104. At this point, the implanter stops rotating the inner sheath 116. If the distal tip 218 is placed in close proximity to the heart surface 106, the pulsing heart surface 106 will bump against the distal tip 218 causing the indicator 302 to appear and disappear, notifying the implanter that the distal tip 218 is in close proximity to the heart surface 106. Further, as shown in FIG. 4, the helical spiral threads 306 grip and stabilize the pericardial sac 108, thereby preventing loss of access into the pericardial space. Also, the gripping of the pericardial sac via the threads results in an implementation of the device 102 and method lifting the pericardial sac 108 from the heart surface 106, thereby increasing the virtual space if desired. Displacing the inner sheath 116 proximally after piercing the pericardial sac 108 lifts the pericardial sac 108, as can be understood from FIG. 4.

Figure 5:
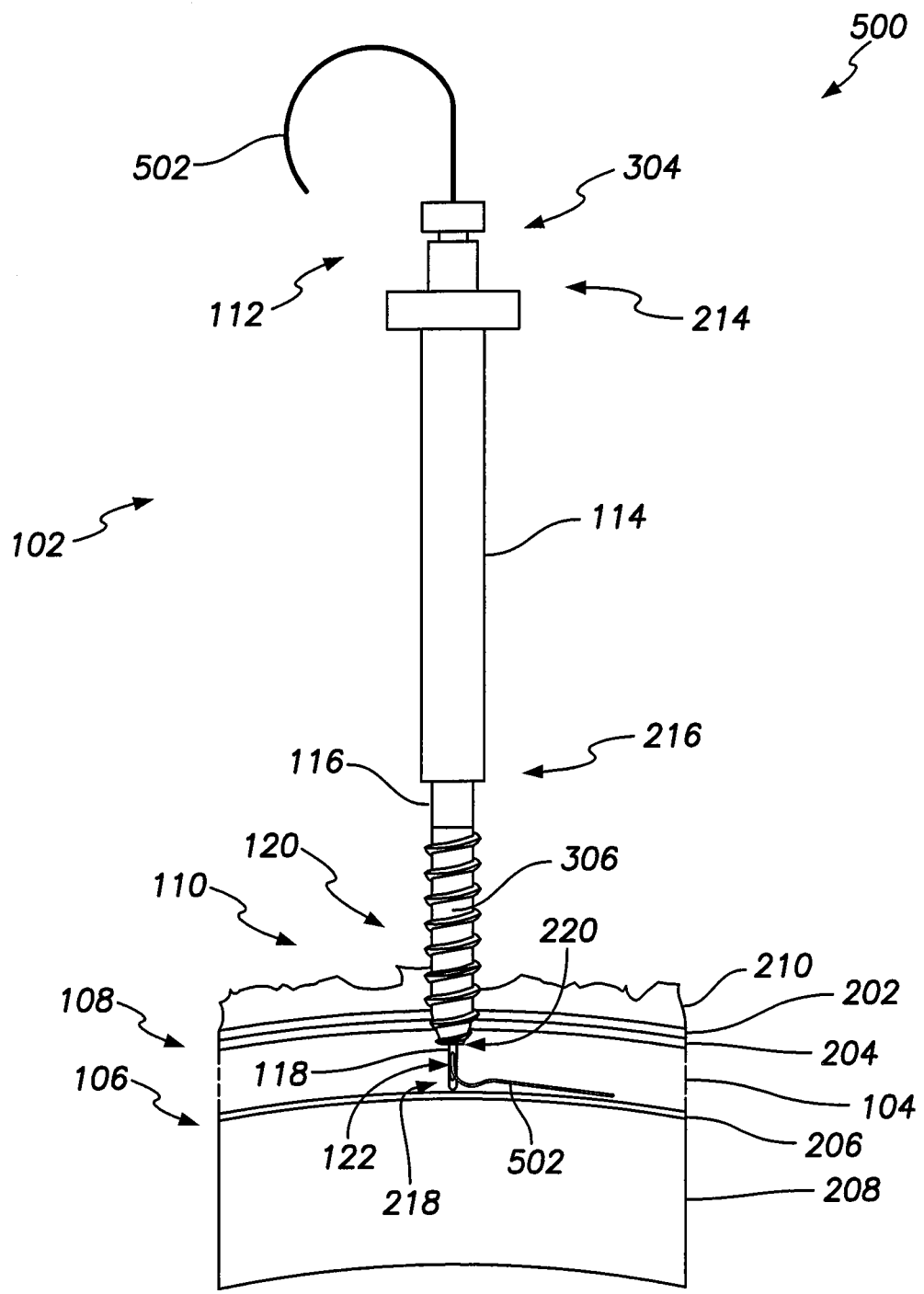
FIG. 5 illustrates the same view as FIG. 2, except the guidewire has been deployed.

As depicted in FIG. 5, a guidewire 502 may be deployed through the opening 122 of the distal tip 218 into the intra-pericardial space 104. The device 102 is adapted to accept the guidewire 502 at the proximal end 112 of the device 102 into the proximal portion 304 of the nose shaft 118. The guidewire 502 is advanced through the lumen of the nose shaft 118 and exits the nose shaft 118 through the opening 122 into the intra-pericardial space 104. Once positioning of the guidewire 502 in the intra-pericardial space 104 has been confirmed, the inner sheath 116 may be axially rotated to disengage the device 102 from the pericardial sac 108. For example, in one implementation, the inner sheath 116 is rotated counterclockwise to disengage the device 102 from the pericardial sac 108. Once the device 102 is disengaged from the pericardial sac 108, the device 102 may be removed from the patient, leaving the guidewire in place for further procedures.

Figure 6:
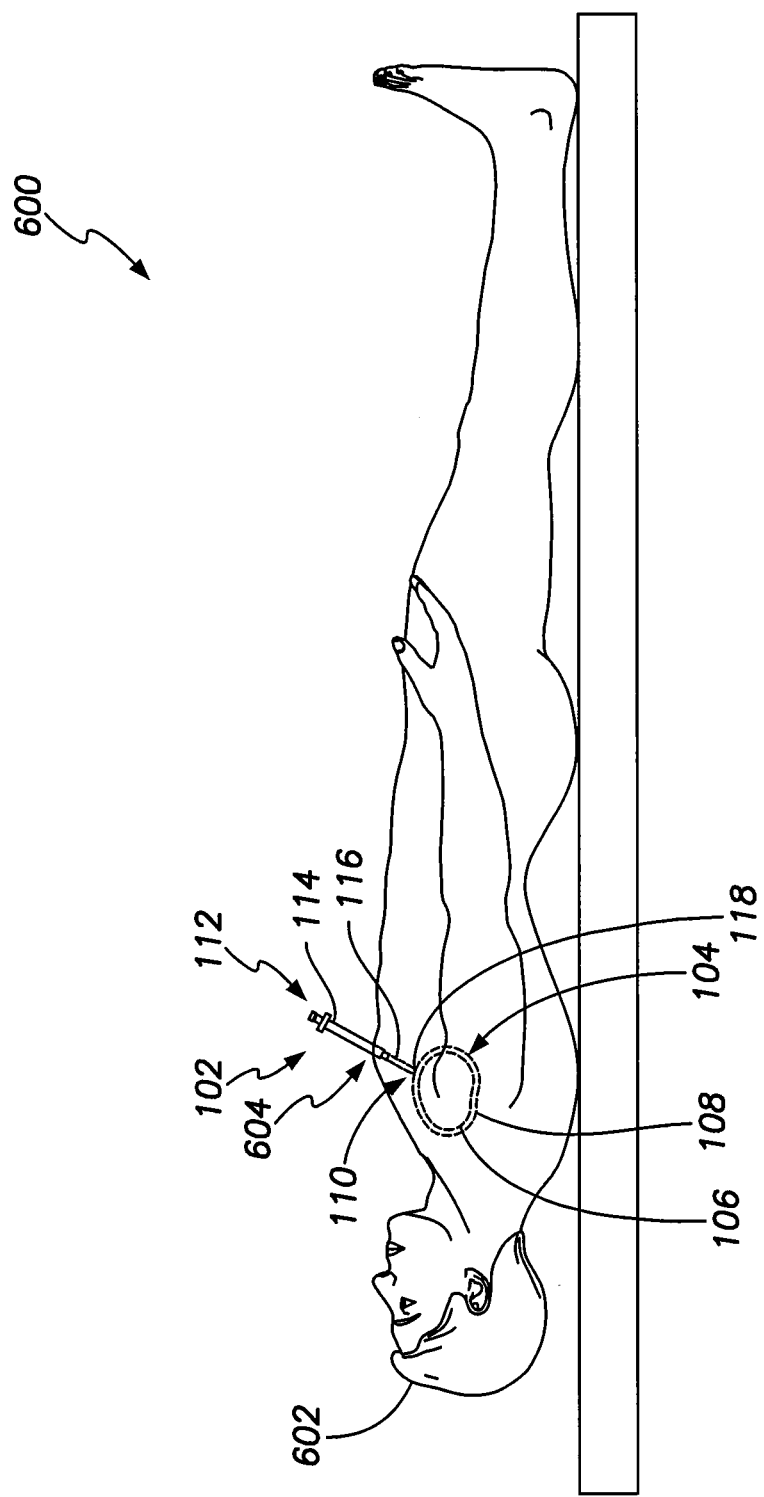
FIG. 6 illustrates a side elevation view of a patient with the distal end of the device inserted into the patient via a sub-xiphoid access.

FIG. 6 illustrates a side elevation view 600 of a patient 602 with the distal end 110 of the device 102 inserted into the patient 602 via a sub-xiphoid access 604. However, those of ordinary skill in the art will recognize the device 102 may be inserted into the patient 602 using other minimally invasive access, including, but not limited to, a transthoracic keyhole access.

As can be understood from FIGS. 1-5, after insertion, the distal portion 120 of the inner sheath 116 is positioned against a surface of the pericardial sac 108 such that the hook 1202 on the distal portion 120 of the inner sheath 116 engages the pericardial sac 108 and the nose shaft 118 is pushed into the confines of the distal portion 120 and the indicator 302 is caused to appear at the proximal end 304. The inner sheath 116 is rotationally displaced relative to the outer sheath 114 by way of the middle sheath 212 until the distal edge 220 cuts through the tissue to free the nose shaft 118 to distally protrude from the distal edge 220 and through the tissue, causing the indicator 302 to displace distally relative to the proximal end 112 of the middle sheath 212. The displacement of the indicator 302 identifies when the distal tip 218 of the nose shaft 118 is positioned in the intra-pericardial space 104. As a result, controlled access to the intra-pericardial space 104 is provided, as depicted in FIG. 4, which illustrates such an occurrence.

The intra-pericardial space 104 may then be accessed to allow implantation of a medical device, such as a stimulating lead. For example, as depicted in FIG. 5, the guidewire 502 may be routed through the lumen of the nose shaft 118 and into the intra-pericardial space 104 to later deposit a pacing or defibrillation lead on the heart surface 106. Once the guidewire 502 is routed to the heart surface 106, the inner sheath 116 may be axially rotated to release the pericardial sac 108. The device 102 is then withdrawn from the patient 602, leaving the guidewire 502 in place, which can then be used to implant the stimulating lead via the use of catheters and/or introducer sheaths tracked into the intra-pericardial space 104 over the guidewire 502.

Figure 7:
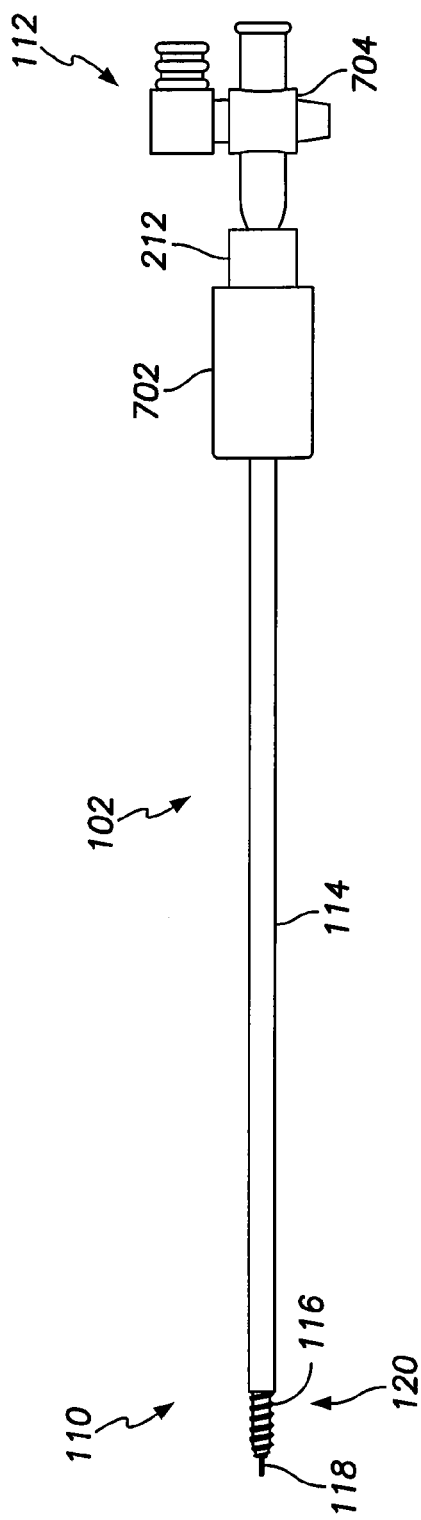
FIG. 7 illustrates a side view of an implementation of the device at rest.

For a detailed discussion of an implementation of the device 102 and method, reference is made to FIG. 7, which is a side view of the device 102 at rest. As shown in FIG. 7, in one implementation, the device 102 includes the outer sheath 114, the inner sheath 116, and the nose shaft 118. The inner sheath 116 includes the distal portion 120, which is adapted to pierce body tissue, such as the pericardial sac 108. In one implementation, the device 102 further includes a grip portion 702 coupled to the proximal end 214 of the outer sheath 114. The middle sheath 212 is adapted to rotate to cause the inner sheath 116 to rotationally and longitudinally displace relative to the outer sheath 114. The grip portion 702 provides stability during this motion.

In one implementation, a luer lock valve 704 is connected to the proximal portion 304 of the nose shaft 118 at the proximal end 112 of the device 102. Contrast can be injected into the luer lock valve 704 to visualize during fluoroscopy. The nose shaft 118 extends through a lumen defined by the inner sheath 116, which extends through a lumen defined by the outer sheath 114. Thus, the nose shaft 118, the inner sheath 116, and the outer sheath 114 are concentrically arranged relative to each other.

Figure 8:
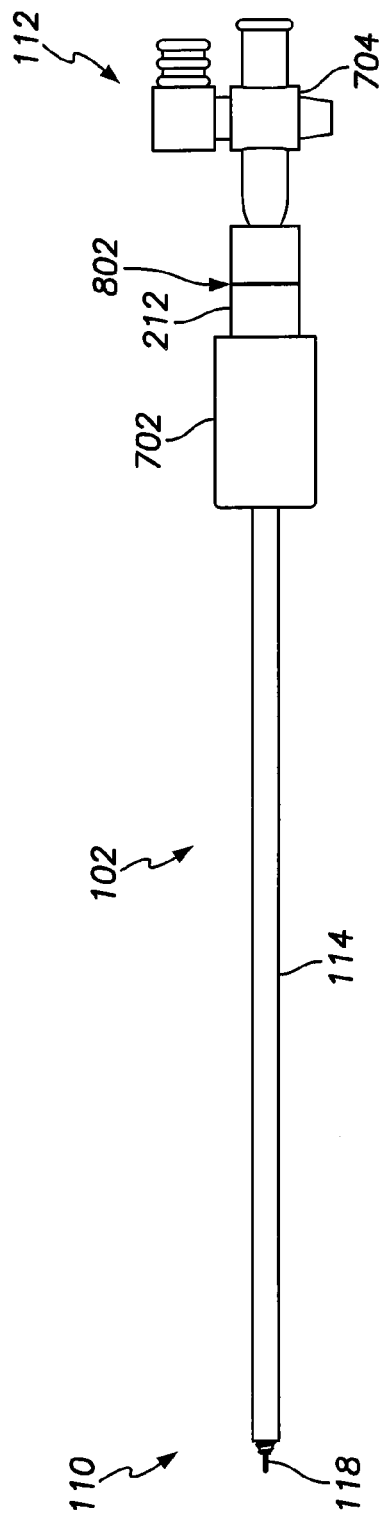
FIG. 8 illustrates the same view as FIG. 7, except the outer sheath has been displaced distally.
Figure 9:
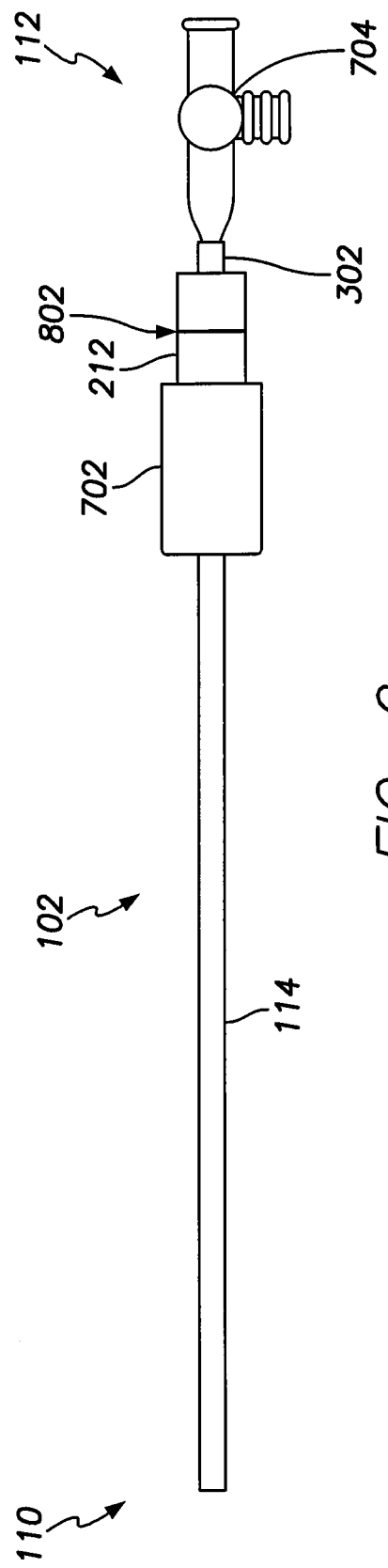
FIG. 9 illustrates the same view as FIG. 7, except the nose shaft has been displaced proximally.

As can be understood from FIGS. 8 and 9, which are, respectively, side views of the device 102 with the outer sheath 114 displaced distally and with the nose shaft 118 displaced proximally, the inner sheath 116 is longitudinally displaceable within the lumen of the outer sheath 114, and the nose shaft 118 is longitudinally displaceable within the lumen of the inner sheath 116. Accordingly, as depicted in FIG. 8, the outer sheath 114 may be moved distally such that the inner sheath 116 is substantially located within the outer sheath 114 and a position marker 802 (i.e., the position marker 802 associated with the inner sheath 116) is exposed on the middle sheath 212. Stated differently, the position maker 802 displaces proximally such that the position maker 802 on the middle sheath 212 is visible outside the grip portion 702. As depicted in FIG. 9, the inner sheath 116 and nose shaft 118 are displaced proximally within the outer sheath 114 causing the indicator 302 of the proximal portion 304 of the nose shaft 118 to displace proximally. In other words, the indicator 302 displaces proximally such that the indicator 302 is visible outside the middle sheath 212.

Figure 12:
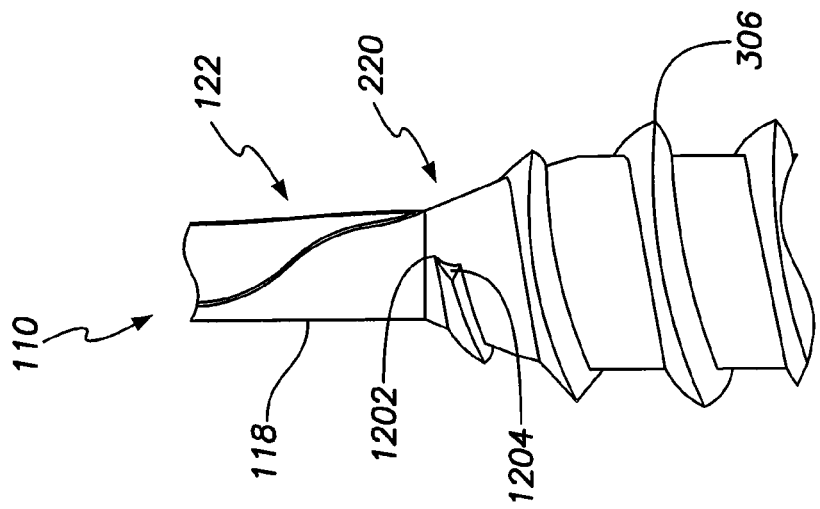
FIG. 12 illustrates a side view of a portion of an implementation of the distal portion of the inner sheath and of the nose shaft.
Figure 11:
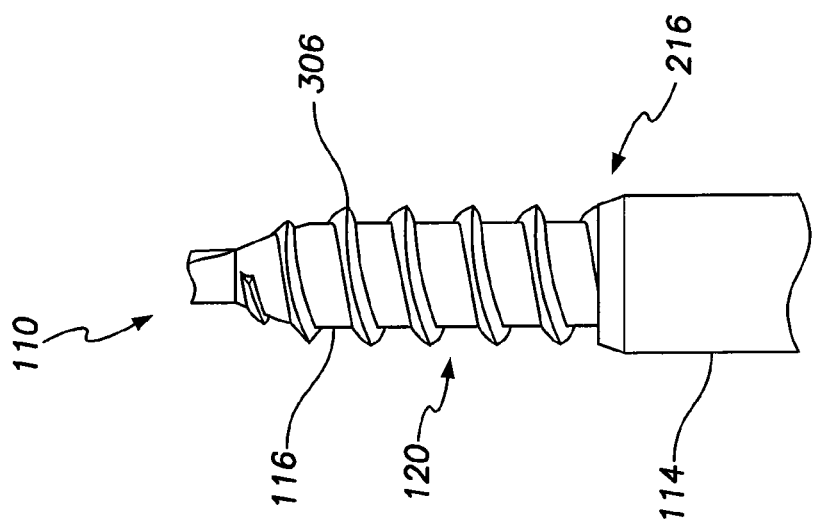
FIG. 11 illustrates a side view of a portion of an implementation of the inner sheath and outer sheath.
Figure 10:
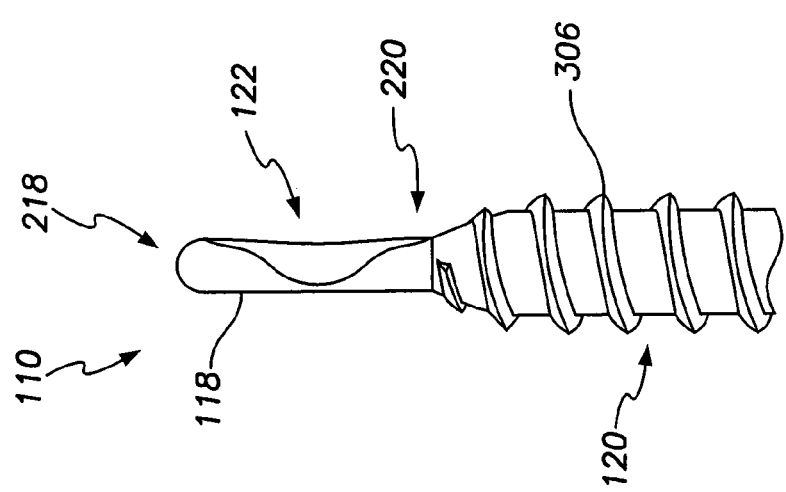
FIG. 10 illustrates a side view of a portion of an implementation of the inner sheath and distal tip of the nose shaft.

FIGS. 10-12 each illustrate a side view of a portion of an implementation of the distal end 110 of the device 102. As depicted in FIG. 10, the distal end of 110 of the device 102 includes the distal tip 218 of the nose shaft 118 and the distal portion 120 of the inner sheath 116. The distal portion 120 is adapted to pierce body tissue, such as the fat layer 210 and the pericardial sac 108. In one implementation, the distal portion 120 includes helical spiral threads 306, and the distal portion 120 is rotated such that the helical spiral threads cut and advance through the body tissue. The distal portion 120 distally terminates at the distal edge 220, and the nose shaft 118 distally terminates with the distal tip 218, which is a blunt surface. The nose shaft 118 is adapted to longitudinally displace relative to the distal edge 220. In one implementation, the distal tip 218 is spring loaded so as to remain protruding out of the distal edge 220 of the distal portion 120 until the distal tip 218 is met with resistance from body tissue, such as the pericardial sac 108. The nose shaft 118 further includes the opening 122, which exposes the lumen of the nose shaft 118, through which the guidewire 502 or other medical device may be deployed.

As can be understood from FIG. 11, which illustrates a side view of the inner sheath 116 and outer sheath 114, the inner sheath 116 extends through the lumen of the outer sheath 114. The outer sheath 114 distally terminates at the distal end 216. In one implementation, the distal end 216 tapers distally creating a cutting edge for easier advancement of the outer sheath through tissue. The distal portion 120 is adapted to displace rotationally and longitudinally relative to the distal end 216. Accordingly, as depicted in FIG. 11, the distal portion 120 can be extended from the outer sheath 114 such that the helical spiral threads 306 are substantially or even completely located past the distal end 216. Additionally, the distal portion 120 can be retracted into the outer sheath 114 such that the helical spiral threads 306 are substantially located within the outer sheath 114.

FIG. 12 illustrates a side view of a portion of the distal portion 120 of the inner sheath 116 and a portion of the nose shaft 118. In one implementation, the distal portion 120 includes the hook 1202, which is adapted to engage body tissue, such as the pericardial sac 108, when the nose shaft 118 is retracted into the inner sheath 116 relative to the distal edge 220. The helical spiral threads 306 include a cutting surface 1204 connected to the hook 1202. In one implementation, the hook 1202 is an extension of one of the helical spiral threads 306 and is partially defined by the cutting surface 1204 defined in the distal edge 220 and the helical spiral threads 306. After the hook 1202 engages the body tissue, the distal portion 120 may be axially rotated causing the cutting surface 1204 to cut through the body tissue. Thus, the hook 1202, the helical spiral threads 306, and the cutting surface 1204 can work together to cause the distal portion 120 of the inner sheath 116 to screw through body tissue.

Figure 13:
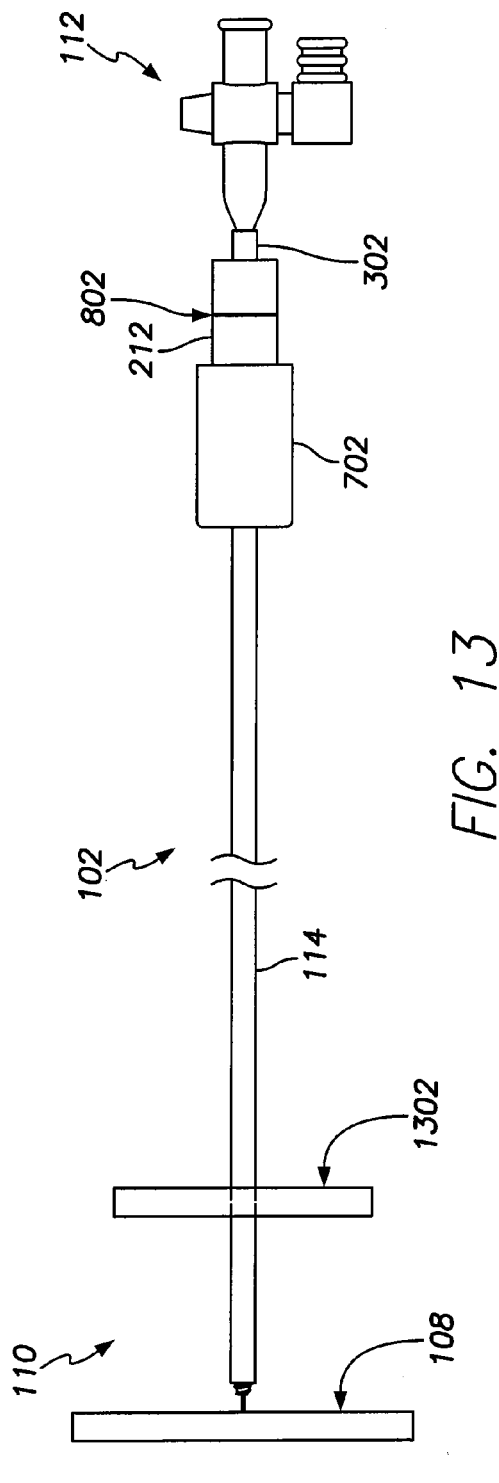
FIG. 13 illustrates a side view of an implementation of the device inserted through the body tissue and has engaged the pericardium.
Figure 14:
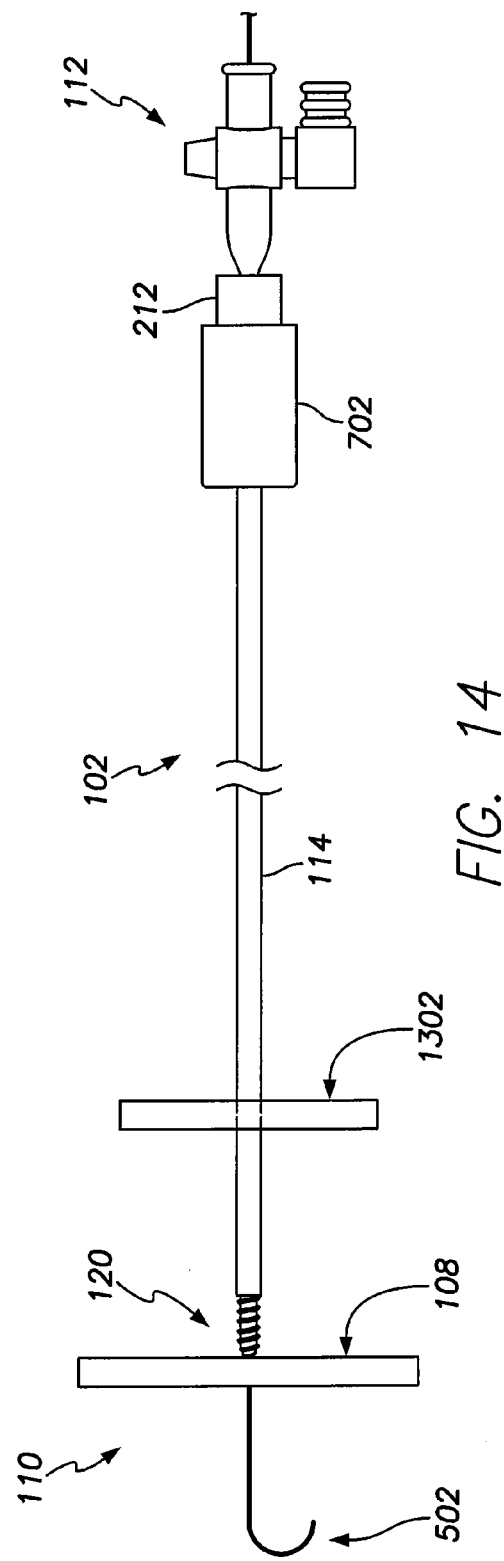
FIG. 14 illustrates the same view as FIG. 13, except the distal tip of the nose shaft has pierced the pericardium and the guidewire has been deployed.

As can be understood from FIGS. 13-14, which each illustrate a side view of an implementation of the device 102 being employed, the device 102 may be inserted through body tissue 1302 to pierce the pericardial sac 108 to deploy the guidewire 502. As depicted in FIG. 13, after the distal portion 120 engages the pericardial sac 108, thereby displacing the indicator 302 and the position marker 802, the inner sheath 116 may be axially rotated relative to the outer sheath 114 using the middle sheath 212. The indicator 302 and the position marker 802 will remain extended from the outer sheath 114 until the nose shaft 118 and the distal portion 120 have respectively penetrated through the pericardial sac 108. The indicator 302 and the position marker 802 will then displace distally, thereby disappearing from view, as shown in FIG. 14. The distal displacements of the indicator 302 and the position marker 802 within the respective confines of the middle sheath 212 and the grip portion 702 identify when the distal tip 218 of the nose shaft 118 is positioned in the intra-pericardial space 104 and the distal portion 120 has threaded through the pericardial sac 108. The guidewire 502 may then be routed through the lumen of the nose shaft 118 and into the intra-pericardial space 104, as depicted in FIG. 14.

Various modifications and additions can be made to the exemplary embodiments discussed without departing from the spirit and scope of the presently disclosed technology. For example, while the embodiments described above refer to particular features, the scope of this disclosure also includes embodiments having different combinations of features and embodiments that do not include all of the described features. Accordingly, the scope of the presently disclosed technology is intended to embrace all such alternatives, modifications, and variations together with all equivalents thereof.

What is claimed is:

1. A medical device adapted for controlled penetration into an intra-pericardial space between a pericardial sac and a heart surface, the medical device comprising:
   an outer sheath comprising a proximal end, a distal end, and a lumen extending between the proximal end and the distal end;
   an inner sheath extending through the lumen of the outer sheath, the inner sheath comprising a distal portion adapted to pierce the pericardial sac;
   wherein the distal portion of the inner sheath comprises helical spiral threads having a cutting surface, the cutting surface adapted to cut the pericardial sac as the inner sheath is axially rotated to longitudinally displace the inner sheath relative to the outer sheath; and
   a nose shaft adapted to displace relative to a distal edge of the distal portion of the inner sheath, wherein longitudinally displacing the distal portion of the inner sheath relative to the outer sheath until the nose shaft displaces relative to the distal edge provides controlled penetration into the intra-pericardial space;
   wherein a distal tip of the nose shaft retracts into the distal edge of the distal portion of the inner sheath when met with resistance from the pericardial sac as the inner sheath is displaced longitudinally; and
   wherein the distal tip of the nose shaft is spring loaded so as to remain protruding from the distal portion of the inner sheath until met with resistance, and
   wherein the distal tip of the nose shaft includes an opening defined therein and through which a guidewire can extend into the intra-pericardial space from within the nose shaft.

2. The medical device of claim 1, wherein an indicator located on a proximal portion of the nose shaft is adapted to displace proximally relative to a proximal end of a middle sheath coupled to the inner sheath, the indicator identifying when the distal tip of the nose shaft is retracted.

3. The medical device of claim 1, further comprising a hook connected to the cutting surface, wherein the retraction of the distal tip of the nose shaft exposes the hook on the distal portion of the inner sheath, the hook adapted to engage the pericardial sac.

4. The medical system of claim 1, wherein the distal tip of the nose shaft is adapted to displace distally relative to the distal edge of the distal portion of the inner sheath causing an indicator located on a proximal portion of the nose shaft to displace distally relative to the proximal end of a middle sheath coupled to the inner sheath, the displacement of the indicator identifying when the distal tip of the nose shaft is positioned in the intra-pericardial space.

5. The medical system of claim 1, wherein the distal tip of the nose shaft comprises a blunt surface, the distal tip of the nose shaft preventing the distal portion of the inner sheath from engaging the surface of the heart.

* * * * *